US008919346B2

(12) United States Patent
Carlin

(10) Patent No.: US 8,919,346 B2
(45) Date of Patent: Dec. 30, 2014

(54) FOREARM AND HAND POSITIONING DEVICE

(76) Inventor: Jennifer Bennett Carlin, Richmond, VA (US)

( * ) Notice: Subject to any disclaimer, the term of this patent is extended or adjusted under 35 U.S.C. 154(b) by 84 days.

(21) Appl. No.: 13/472,722

(22) Filed: May 16, 2012

(65) Prior Publication Data

US 2013/0037036 A1 Feb. 14, 2013

Related U.S. Application Data

(60) Provisional application No. 61/522,724, filed on Aug. 12, 2011.

(51) Int. Cl.
*A61G 15/00* (2006.01)
*A61F 5/00* (2006.01)
*A61G 13/12* (2006.01)
*A61G 7/10* (2006.01)

(52) U.S. Cl.
CPC .......... *A61G 13/1235* (2013.01); *A61G 13/124* (2013.01); *A61G 7/1021* (2013.01)
USPC .............................................. 128/845; 602/13

(58) Field of Classification Search
USPC ............. 602/13; 128/845, 877, 869; 600/217, 600/183, 37, 490; 5/630, 644, 713, 5/623–624, 646, 650; 601/151–152; 606/201–203, 240–241
See application file for complete search history.

(56) References Cited

U.S. PATENT DOCUMENTS 2,266,230 A 12/1941 Mazzeo et al.
3,153,413 A * 10/1964 Gottfried ........................ 602/60
3,242,923 A * 3/1966 Jacoby, Sr. ..................... 128/877
3,762,401 A 10/1973 Tupper
4,628,911 A * 12/1986 Bornstein ....................... 602/20
4,637,377 A 1/1987 Loop
4,809,684 A * 3/1989 Gardner et al. ............... 601/152
4,909,264 A 3/1990 Wadsworth, III et al.
5,025,801 A 6/1991 Callaway
5,190,530 A * 3/1993 Greeff et al. .................. 604/179
5,601,597 A * 2/1997 Arrowood et al. ............ 606/203
5,727,559 A * 3/1998 Hynson et al. ................ 600/485
5,813,977 A 9/1998 Hinchliffe et al.
5,997,495 A * 12/1999 Cook et al. ...................... 602/62
6,065,166 A 5/2000 Sharrock et al.
6,544,253 B1 4/2003 Tanner
7,017,215 B1 * 3/2006 Singer et al. ....................... 5/646
7,168,116 B2 1/2007 Reger et al.
7,802,333 B2 9/2010 Marguet et al.
8,454,542 B2 * 6/2013 Hirata et al. .................. 601/150

* cited by examiner

*Primary Examiner* — Justine Yu
*Assistant Examiner* — Ophelia A Hawthorne
(74) *Attorney, Agent, or Firm* — Antonelli, Terry, Stout & Kraus, LLP.

(57) ABSTRACT

A radial artery of a patient is made accessible to an operator on the right side of the patient for performing a left radial artery accessed cardiac catheterization with a forearm and hand positioning device which includes first and second inflatable air bladders. The first air bladder extends longitudinally with an upper surface that, when the air bladder is inflated, supports and positions the forearm and hand of a patient with a radial artery of the patient remaining accessible to the operator. The second air bladder extends longitudinally beneath and is connected to the first air bladder and when inflated elevates the first air bladder and a forearm and hand of the patient held therein above a support for the patient's arm.

10 Claims, 4 Drawing Sheets

FOREARM AND HAND POSITIONING DEVICE

RELATED APPLICATION

This application claims priority under 35 U.S.C. §119 of U.S. provisional application No. 61/522,724 filed Aug. 12, 2011. The disclosure of provisional application No. 61/522,724 is incorporated by reference herein in its entirety.

TECHNICAL FIELD

The present invention is a forearm and hand positioning device to secure the forearm and hand in a stable position while the patient undergoes a radial artery accessed cardiac catheterization.

BACKGROUND AND SUMMARY

Radial artery accessed catheterizations are being performed with increasing frequency. It is important during these procedures that the patient's arm be maintained in stable, accessible position. This can be difficult to achieve where the arm is merely supported on a cath arm board. With the operator on the right side of the patient, for a left radial artery accessed cardiac catheterization the problem is compounded in that the operator may have to lean over the patient for accessing the radial artery. There is a need for a forearm and hand positioning device for maintaining a radial artery of a patient in the correct accessible position while the patient undergoes a radial artery accessed cardiac catheterization. The present invention addresses this need.

A forearm and hand positioning device according to a preferred embodiment of the invention comprises a first inflatable air bladder longitudinally extending with an upper surface that, when the first air bladder is inflated, supports the forearm and hand of a patient with a radial artery of the patient remaining accessible to an operator. A second air bladder of the device longitudinally extends beneath and is connected to the first air bladder and is configured when the second air bladder is inflated, to elevate the first air bladder and a forearm and hand supported on the first air bladder to a comfortable working height for an operator above a support for the patient's arm.

The first air bladder is preferably configured to surround most of a patient's forearm when the first air bladder is inflated for securing the patient's arm on the device. In the example embodiment the first air bladder surrounds at least approximately 75% of the forearm in an area above the proximal forearm/wrist of the patient. The air bladders in a disclosed embodiment have a necked configuration in an intermediate portion along the longitudinal extent of the device between forearm and hand supporting portions for exposing the wrist and radial artery of a patient for access by an operator. A plurality of releasable, adjustable straps are provided on the disclosed embodiment of the device for securing a hand, forearm and upper arm of a patient to the device.

The first air bladder in the example embodiment has a length and a configuration for tightening around a portion of both the upper arm and forearm of a patient when the bladder is inflated. The second air bladder has a length coextensive with the first air bladder and extends beneath a portion of the upper arm, forearm and hand of a patient secured on the first air bladder. The second air bladder, when inflated, is wedge shaped in the longitudinal direction of the device with increasing thickness in a direction from the arm toward the forearm and hand supporting portions.

These and other features and advantages of the invention will become more apparent from the following detailed description of an example embodiment of the invention taken with the accompanying drawings.

DETAILED DESCRIPTION

Figure 1:
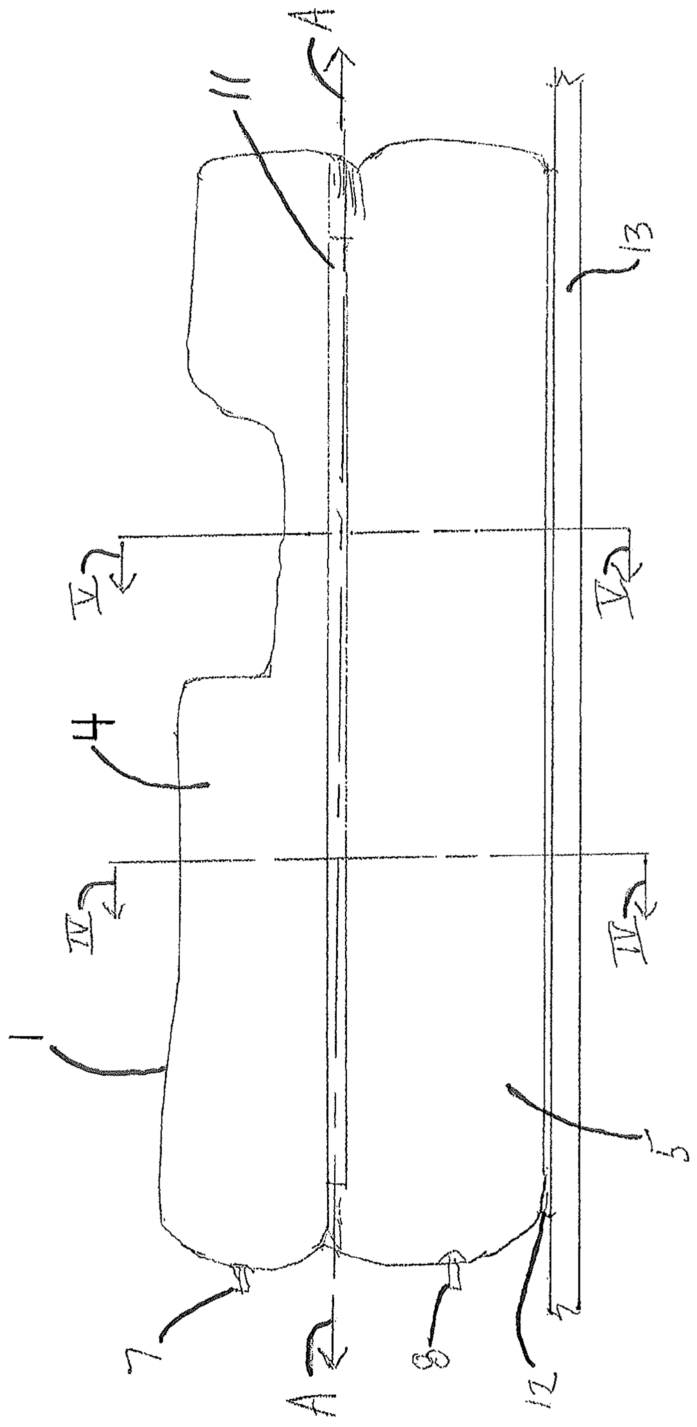
FIG. 1 is a side view of an example embodiment of a forearm and hand positioning device according to the invention shown supported on a cath arm board for maintaining a radial artery of a patient in the correct accessible position while the patient undergoes a radial artery accessed cardiac catheterization.
Figure 2:
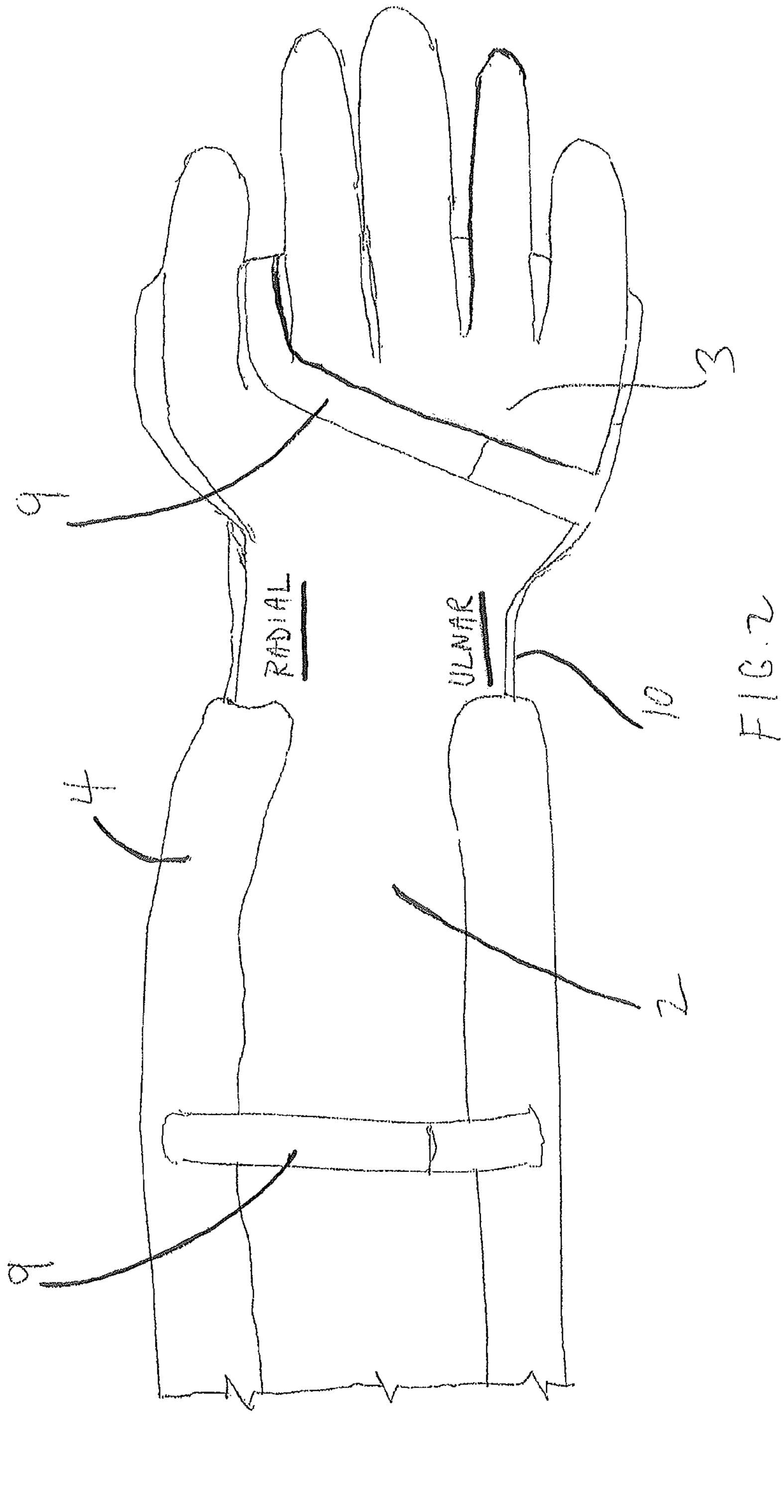
FIG. 2 is a top view of the proximal portion of the device of FIG. 1 shown with the left forearm and hand of a patient secured in a stable position in the device by a first air bladder of the device around the arm and by releasable Velcro straps about the hand and arm leaving the upwardly facing portions of the hand and proximal forearm exposed for accessing the radial artery.

The purpose of the device 1 of the example embodiment shown in FIGS. 1-5 is to secure the forearm 2 and hand 3 of a patient in a stable position on a cath arm board/support 13 while the patient undergoes a radial artery accessed cardiac catheterization. The device comprises first and second inflatable air bladders, 4 and 5. The first air bladder 4 is longitudinally extending in the direction of arrow A-A in FIG. 1, and has an upper surface 6 that, when the first air bladder is inflated, supports and tightens around the arm as shown in FIG. 2 to secure the arm in a position in the device. The second air bladder 5 is longitudinally extending beneath and connected to the first air bladder and configured, when the second air bladder is inflated, to elevate the arm above the support 13 to comfortable working height for the operator. The first and second air bladders are separately inflatable using compressed air introduced through respective air valves 7 and 8 shown schematically in FIG. 1. The extent of inflation of air bladder 5 can be varied for adjusting the height the arm is supported above the cath arm board 13 independently of positioning tightness of the air bladder 4 on the arm. Three Velcro® straps 9 on the device, only two of which are shown in the drawings, releasably secure the hand, the proximal forearm and the upper arm near the bicep to the device.

Figure 4:
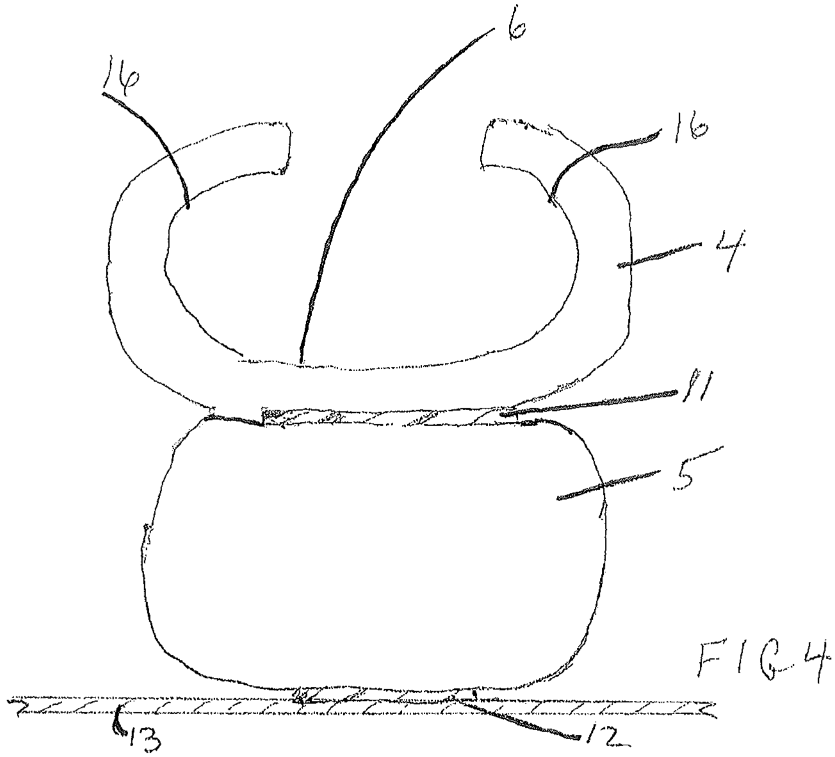
FIG. 4 is a sectional view of the device taken along the line IV-IV in FIG. 1, shown inflated.
Figure 5:
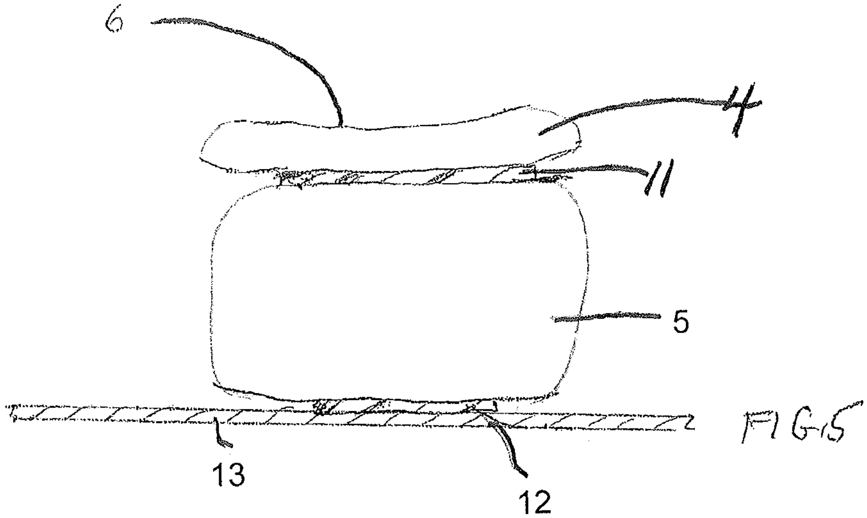
FIG. 5 is a sectional view of the device taken along the line V-V in FIG. 1, shown inflated.

The first air bladder 4 can be adjustably filled or pressurized with compressed air to accommodate small to large sized forearms because it surrounds with its upwardly extending curved wall portions 16 most of the forearm when inflated as shown in FIGS. 2 and 4. The air bladder surrounds approximately 75% of the forearm above the exposed wrist/radial-ulnar and hand in the example embodiment so the patient cannot turn the arm within the device, thereby maintaining the correct accessible position. The hand and proximal end of the forearm/wrist are supported on a necked area 10 of the air bladder 4 but not surrounded by the bladder as shown in FIGS. 2 and 5. The air bladders preferably each extend coextensively to the upper arm so when second air bladder 5 fills the entire arm elevates the one straight unit. The device will be especially helpful when performing a cardiac catheterization from the left radial artery. The operator can remain on the right side of the patient because the device on the left arm secures it in position and elevates the arm so the operator does not have to lean over the patient.

Figure 3:
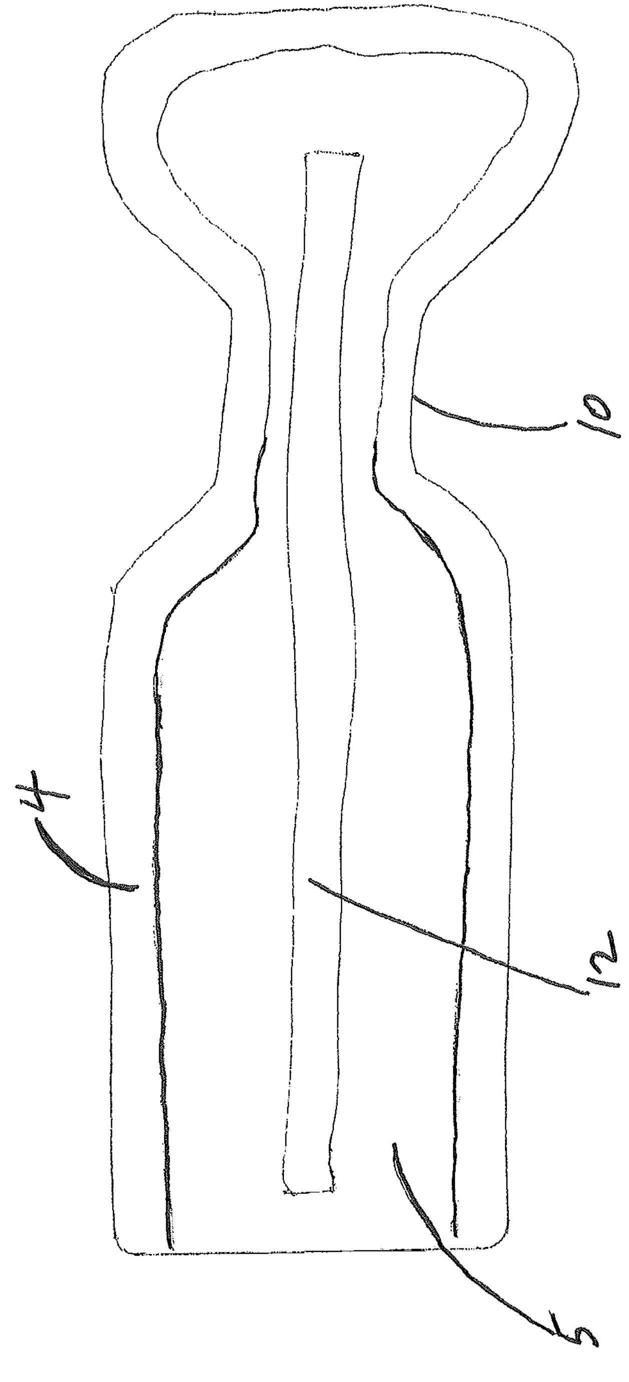
FIG. 3 is a bottom view of the device of FIG. 1 showing a second, lower air bladder of the device for elevating the arm and hand to a comfortable working height for the operator.

One or more longitudinally extending stiffeners/stays 11 can optionally be provided intermediate the two air bladders, or internally in one or both air bladders, for providing additional longitudinal stiffness for maintaining planarity/resisting bending of the arm. An adhesive strip 12 can be provided on the bottom of the second air bladder 5 as shown in FIG. 3. The adhesive strip preferably has a removable/peelable covering which, when removed, exposes the adhesive for releasably anchoring the device on the cath arm board/support 13 as shown in FIG. 1 during a catheterization to prevent shifting of the device on the support. The device can be made of moldable plastic and integrally formed or formed of separate components bonded or fastened together. The lightweight, low cost device is disposable or, where sterilization is possible, can be made reusable. In the example, the height of the second air bladder 5 is tapered or wedge shaped being progressively thicker in the direction of the hand and thinner in the direction of the upper arm as shown in FIG. 1 to adjustably elevate the arm up to at least six inches, for example, or more above the cath arm board upon inflation depending upon the desired/correct accessible position.

While I have shown and described an example embodiment of the invention herein, it is understood that the same is not limited thereto but is susceptible to numerous change and modifications as will be readily understood by the skilled artisan without departing from the scope of the present invention as defined in the appended claims. Therefore, I do not wish to be limited to the details shown and described herein, but instead to cover all such changes and modifications as are encompassed by the scope of the appended claims.

The invention claimed is:

1. A forearm and hand positioning device for use on a support including a cath arm board to secure the forearm and hand of a patient in a stable position while the patient undergoes a radial artery accessed cardiac catheterization, the device comprising:

a first inflatable air bladder longitudinally extending with an upper surface having arm and hand supporting portions that, when the first air bladder is inflated, support and tighten around most of the periphery of the arm in an area above the proximal forearm/wrist of a patient and support the hand of the patient with the radial artery at the proximal forearm/wrist of the patient remaining exposed and accessible to an operator, a second inflatable air bladder longitudinally extending beneath and connected to the first air bladder and configured, when the second air bladder is inflated, to elevate the first air bladder and an arm and hand of a patient supported on the upper surface of the first air bladder above a support for the patient's arm, wherein the first and second air bladders are separately inflatable for independently adjusting the elevation of the patient's arm and hand above the support and the positioning tightness of the first air bladder around a patient's arm.

2. The device of claim 1, wherein the first air bladder has a length and a configuration for tightening around a portion of the upper arm and the forearm of a patient when the first air bladder is inflated.

3. The device according to claim 2, further comprising a plurality of releasable, adjustable straps for securing a hand, forearm and upper arm of a patient on the first air bladder of the device.

4. The device according to claim 2, further comprising at least one longitudinally extending stiffener for maintaining substantial planarity of the forearm and hand positioning device and prohibiting bending of an arm secured on the forearm and hand positioning device.

5. The device of claim 1, further comprising means for releasably connecting the device to a cath arm board.

6. The device of claim 5, wherein the means for releasably connecting includes an adhesive strip on a lower surface of the second air bladder for engaging a cath arm board.

7. The device of claim 1, wherein the first air bladder is configured to surround at least approximately 75% of the patient's forearm in the area above the proximal forearm/wrist of the patient.

8. The device of claim 1, wherein the second air bladder, when inflated, is wedge shaped in a longitudinal direction of the device with increasing thickness in a direction from arm to hand supporting portions.

9. The device of claim 1, wherein the second air bladder has a length sufficient for extending beneath a portion of the upper arm, the forearm and the hand of a patient supported on the first air bladder.

10. The device of claim 1, wherein the first and second air bladders have a necked configuration in an intermediate portion between the arm and hand supporting portions for exposing the wrist and radial artery of a patient for access by an operator.

* * * * *